US005974112A

United States Patent [19]
Reiffel

[11] Patent Number: 5,974,112
[45] Date of Patent: Oct. 26, 1999

[54] METHOD AND APPARATUS TO CONTROL PHOTON BEAM DOSE ENHANCEMENTS

[76] Inventor: Leonard Reiffel, 602 Deming Pl., Chicago, Ill. 60614

[21] Appl. No.: 09/195,337

[22] Filed: Nov. 18, 1998

Related U.S. Application Data

[60] Provisional application No. 60/066,420, Nov. 24, 1997.

[51] Int. Cl.$^6$ ..................................................... A61N 5/10
[52] U.S. Cl. .................... 378/65; 378/145; 250/396 ML; 250/492.3
[58] Field of Search ................................. 378/65, 64, 68, 378/145; 250/396 ML, 398, 492.3

[56] References Cited

U.S. PATENT DOCUMENTS

| | | | |
|---|---|---|---|
| 4,063,098 | 12/1977 | Enge | 250/398 |
| 4,134,017 | 1/1979 | Azam et al. | 250/398 |
| 5,267,294 | 11/1993 | Kuroda et al. | 378/65 |
| 5,883,934 | 3/1999 | Umeda | 378/64 |

OTHER PUBLICATIONS

C.C. Shih, "High Energy Electron Radiotherapy in a Magnetic Field," Medical Physics, vol. 2, No. 1, Jan./Feb. 1975, pp. 9–13.

Whitmire, D P., Bernard, D. L., Peterson, MD, and Purdy, J. A., "Magnetic Enhancement of Electron Dose Distribution in a Phantom," Medical Physics, vol. 4, No. 2, Mar./Apr. 1977, pp. 127–131.

Nath, R. and Schulz, R. J., "Modification of Electron–beam Dose Distributions by Transverse Magnetic Fields," Medical Physics, vol. 5, No. 3, May/Jun. 1978, pp. 226–230.

Whitmire, D. P. Bernard, D. L. and Peterson, M.D., "Magnetic Modification of the Electron–Dose Distribution in Tissue and Lung Phantoms," Medical Physics, vol. 5, No. 5, Sep./Oct. 1978, pp. 409–417.

Paliwal, B. R., Wiley, Jr., A. L., Wessels, B. W. and Choi, M. C., "Magnetic Field Modification of Electron–beam Dose Distributions in Inhomogeneous Media," Medical Physics, vol. 5, No. 5 Sep./Oct. 1978, pp. 404–408.

Paliwal, B. R., Thomadsen, B. R. and Wiley, Jr., A. J., "Magnetic Modification of Electron Beam Dose Distributions," Acta Radiological Oncology, vol. 18, 1979 Fasc. 1, pp. 57–64.

Weinhous, M. S., Nath, R. and Schuylz, R. J., "Enhancement of Electron Beam Dose Distributions by Longitudinal Magnetic Fields: Monte Carlo Simulations and Magnet System Optimization," Medical Physics, vol. 12, No. 5 Sep./Oct. 1985, pp. 598–603.

*Primary Examiner*—David P. Porta
*Assistant Examiner*—Drew A. Dunn
*Attorney, Agent, or Firm*—Don Moyer

[57] ABSTRACT

A photon beam dose enhancement is controlled by configuring a topical magnetic field, the magnetic field configuration having a magnetic field component across the beam path and having a magnetic field gradient component along the beam path which cause the dose enhancement, the dose enhancement being changeable during beam use by changing the magnetic field configuration during beam use, wherein the topical magnetic field can be produced by an array of magnet coils.

21 Claims, 5 Drawing Sheets

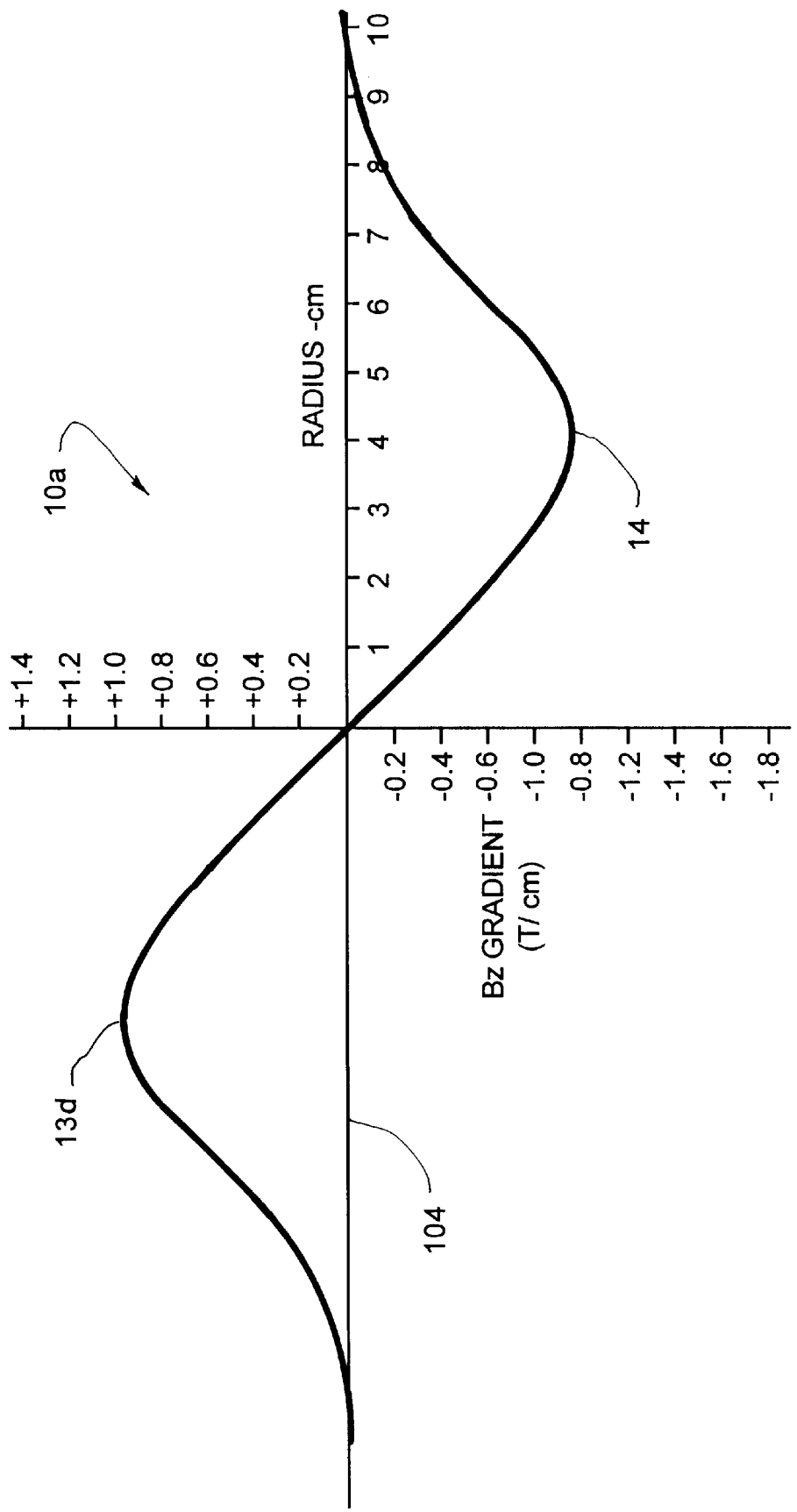

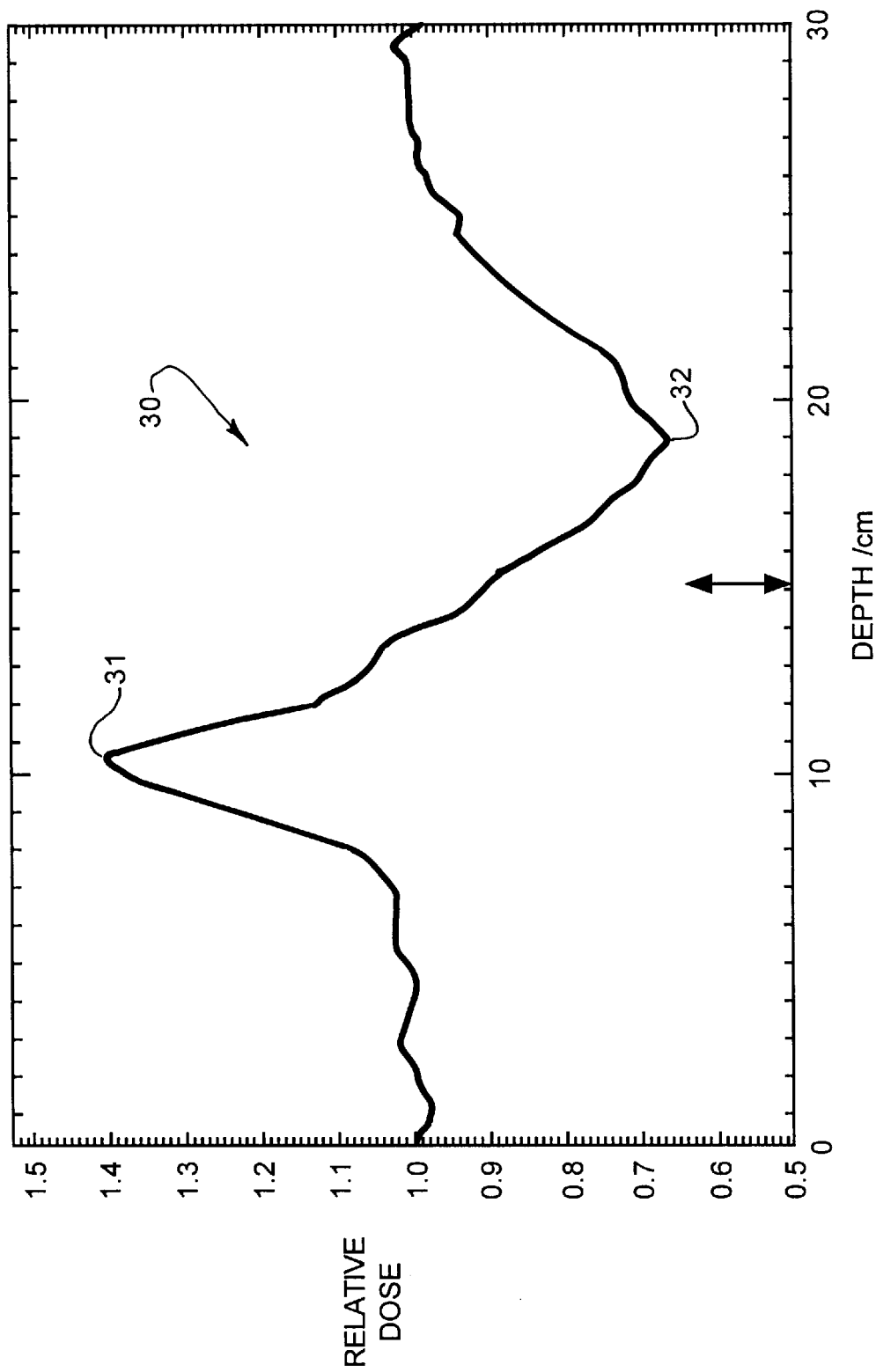

METHOD AND APPARATUS TO CONTROL PHOTON BEAM DOSE ENHANCEMENTS

CROSS REFERENCES TO RELATED APPLICATIONS

This application claims benefit of U.S. Provisional Application No. 60/066,420 filed Nov. 24, 1997.

STATEMENT AS TO RIGHTS TO INVENTIONS MADE UNDER FEDERALLY SPONSORED RESEARCH AND DEVELOPMENT

BACKGROUND OF THE INVENTION

The invention is used to control dose enhancements along a photon beam path by control of the magnetic field configuration of a topical magnet, the magnetic field configuration having a magnetic field component across the photon beam path and having a magnetic field gradient component along the photon beam path.

Since the advent of radiation systems workers have long been seeking methods and devices to control dose enhancements, where a dose enhancement is the ratio of radiation dose in a target volume relative to the radiation dose outside of the target volume. For example, one of the fundamental problems in the treatment of many forms of cancer using beams of high energy photons (mainly in the range 1 MEV to 60 MEV) from accelerators and other sources is the limited success of current techniques for delivering appropriate levels of dose to a diseased region while sparing surrounding healthy tissue.

The dose generated by a high energy photon beam comes from the loss of energy of Compton and pair production electrons in an electron-photon cascade generated by the photon beam. (The differences in charge and particle interactions between electrons and positrons are minimal in the phenomena relied on here, so positrons created by pair production are called simply electrons here.) The electron-photon cascade follows the photon beam progression, and scattering into the penumbral region around the beam is usually acceptably small. Thus, healthy regions lying in directions transverse to the beam direction can usually be protected by shaping the photon beam cross-section by means of absorber blocks and related techniques. In addition, the targeted region, when possible, is irradiated from various directions so as to spare any particular region of surrounding healthy or especially radiosensitive tissue from the full destructive impact of the treatment. For a photon beam incident from any given direction, however, there heretofore has been no effective means of minimizing damage to healthy tissue not in the target volume. No suggestions have been made that dose enhancements along uncharged photon beams could be controlled by control of the magnetic field configuration of a topical magnet, the magnetic field configuration having a magnetic field component across the photon beam path and having a magnetic field gradient component along the photon beam path.

Suggestions for improving the dose distribution along a charged particle beam by use of magnetic fields have been made. In C. C. Shih, "High Energy Electron Radiotherapy in a Magnetic Field," Medical Physics, Vol. 2, No. 1, January/February 1975 calculations are reported which suggest that an electron beam dose distribution could be improved in the uniform magnetic field of a large magnet. In Whitmire, D. P., Bernard, D. L., Peterson, MD, and Purdy, J. A., "Magnetic Enhancement of Electron Dose Distribution in a Phantom," Medical Physics, Vol. 4, No. 2, March/April 1977 measurements of dose in a phantom in the uniform magnetic field of a large magnet are reported which also suggest that an improved dose distribution could be achieved by these means.

Similar work is reported in Nath, R. and Schulz, R. J., "Modification of Electron-beam Dose Distributions by Transverse Magnetic Fields," Medical Physics, Vol. 5, No. 3, May/June 1978; in Whitmire, D. P. Bernard, D. L. and Peterson, M.D., "Magnetic Modification of the Electron-Dose Distribution in Tissue and Lung Phantoms," Medical Physics, Vol. 5, No. 5, September/October 1978; in Paliwal, B. R., Wiley, Jr., A. L., Wessels, B. W. and Choi, M. C., "Magnetic Field Modification of Electron-beam Dose Distributions in Inhomogeneous Media," Medical Physics, Vol 5, No. 5 September/October 1978; and in Paliwal, B. R., Thomadsen, B. R. and Wiley, Jr., A. J., "Magnetic Modification of Electron Beam Dose Distributions," Acta Radiological Oncology, Vol. 18, 1979 Fasc. 1.

None of these workers suggest that dose enhancements along a photon beam could be controlled by controlling the configuration of a topical magnet magnetic field having a magnetic field component across the photon beam and having a magnetic field gradient component along the photon beam. The 1978 Whitmire paper mentions an increase in dose from a photon beam at the surface of a phantom in their magnetic field and a decrease in dose at the bottom of their phantom. Their discussion of this observation teaches away from control of dose enhancements by control of the configuration of the magnetic field of a topical magnet.

In Weinhous, M. S., Nath, R. and Schuylz, R. J., "Enhancement of Electron Beam Dose Distributions by Longitudinal Magnetic Fields: Monte Carlo Simulations and Magnet System Optimization," Medical Physics, Vol. 12, No. 5 September/October 1985 and in Bielajew, A. F., "The Effect of Strong Longitudinal Magnetic Fields on Dose Deposition from Electron and Photon Beams," Medical Physics, Vol. 20, No. 4, July August 1993 calculations are reported to suggest that large uniform magnetic fields along the beam axis would reduce the scattering of electrons laterally out of the beam. In the case of the photon beam, the electrons in the electron-photon cascade which are scattered transverse to the beam are kept in the beam, thereby somewhat reducing the dose in the penumbral region around the beam. Their discussion of this effect teaches away from using a topical magnet with a gradients along a photon beam path.

SUMMARY OF THE INVENTION

Objects of this invention comprise requirements listed in the following imperatives. Control dose enhancement along a photon beam by control of the configuration of a magnetic field produced by a topical magnet. Configure the magnetic field to a magnetic field configuration with a magnetic field component across the photon beam and with a magnetic field gradient component along the beam which cause the dose enhancement. During use of the beam configure the magnetic field to a second magnetic field configuration with a second magnetic field component across the beam path and with a second magnetic field gradient component along the beam path which cause a second dose enhancement. Use an array of magnet coils to make the topical magnet. Make the array of magnet coils an array of magnet coils on a planar surface and alternatively on a non-planar surface. Make the topical magnet support a method where a dose enhancement is chosen and the magnetic field is configured to cause the dose enhancement and where a second dose enhancement is chosen and during use of the beam the magnetic field configuration is changed to cause the second dose enhancement.

Other objects will be comprehended in the drawings and detailed description, which will make additional objects obvious hereafter to persons skilled in the art.

In summary, one embodiment of this invention is a dose enhancement device used with a photon beam source which produces a photon beam which produces an electron-photon cascade along the beam, the dose enhancement control device being at least one topical magnet having a magnetic field configuration with a magnetic field component across the beam and with a magnetic field gradient along the beam which cause a dose enhancement, the dose enhancement being controlled by control of the magnetic field configuration.

Other equivalent embodiments will be comprehended in the drawings and detailed description, which will make additional equivalent embodiments obvious hereafter to persons skilled in the art.

BRIEF DESCRIPTION OF THE DRAWINGS

FIG. 4 shows the gradient along the magnetic field plotted in FIG. 3,

FIG. 5 shows the dose enhancement along the gradient plotted in FIG. 4.

DESCRIPTION OF THE PREFERRED EMBODIMENTS

Figure 1:
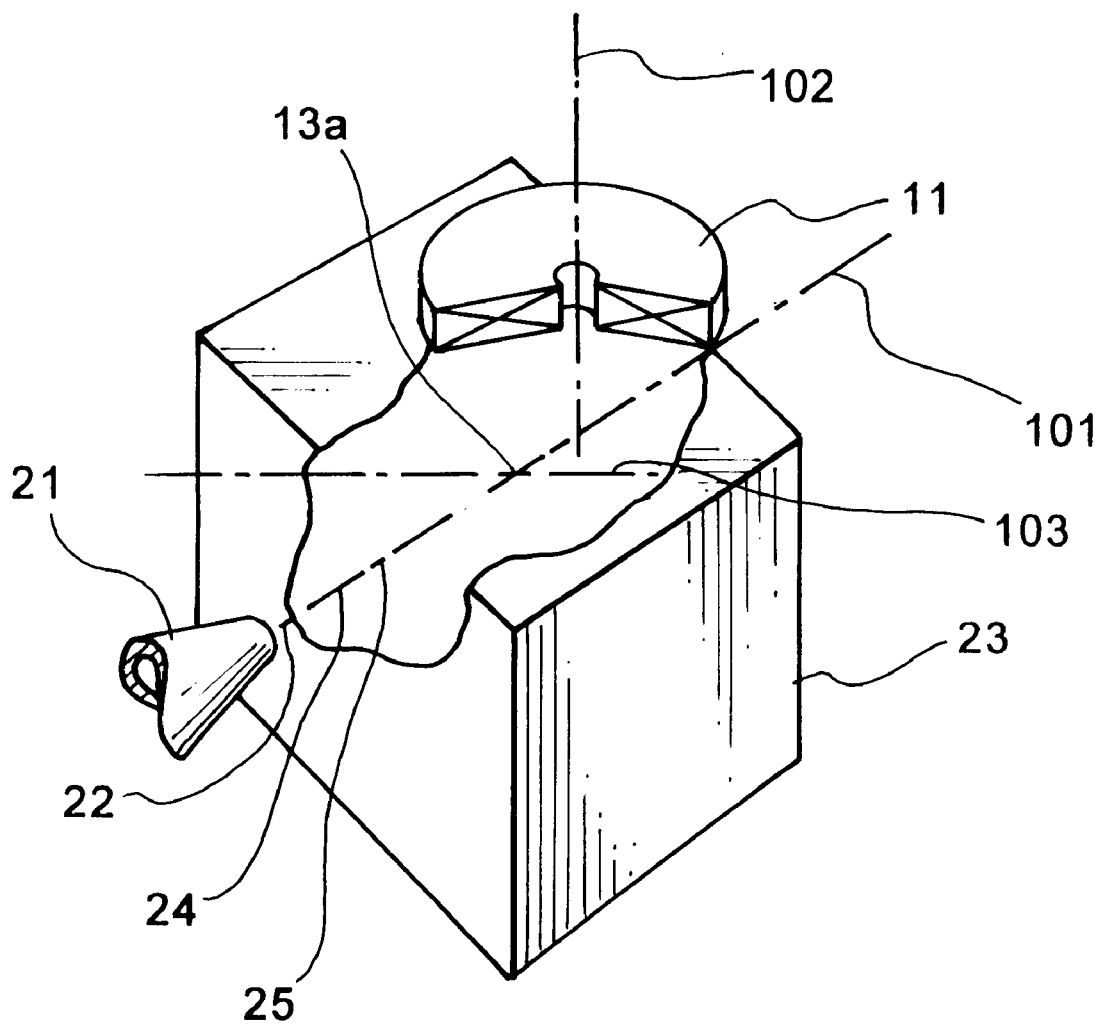
FIG. 1 shows elements of photon beam radiation system with a topical magnet to control a dose enhancement.

The radiation system shown in FIG. 1 has a photon beam source 21 which produces an incident photon beam along a beam path, the beam path being defined by all of the paths of the incident photons in the beam. Though this beam path, can have a complicated cross section, a beam vector 101 can be chosen to represent the beam path. The photon beam is indicated by the point 22 on the beam vector 101. The beam vector 101 enters a body 23 at the point 24 and the incident photons generate an electron-photon cascade along the beam path, the electron-photon cascade being indicated by the point 25 on the beam vector 101 in the body.

At the energies of interest here the path of the electron-photon cascade, being the collection of the paths of the particles in the electron-photon cascade, can be considered to follow along the incident photon beam path. Thus, the electron-photon cascade can also be represented by the beam vector 101, so that beam path here means both the incident photon beam path and the beam path of the electron-photon cascade.

Figure 2:
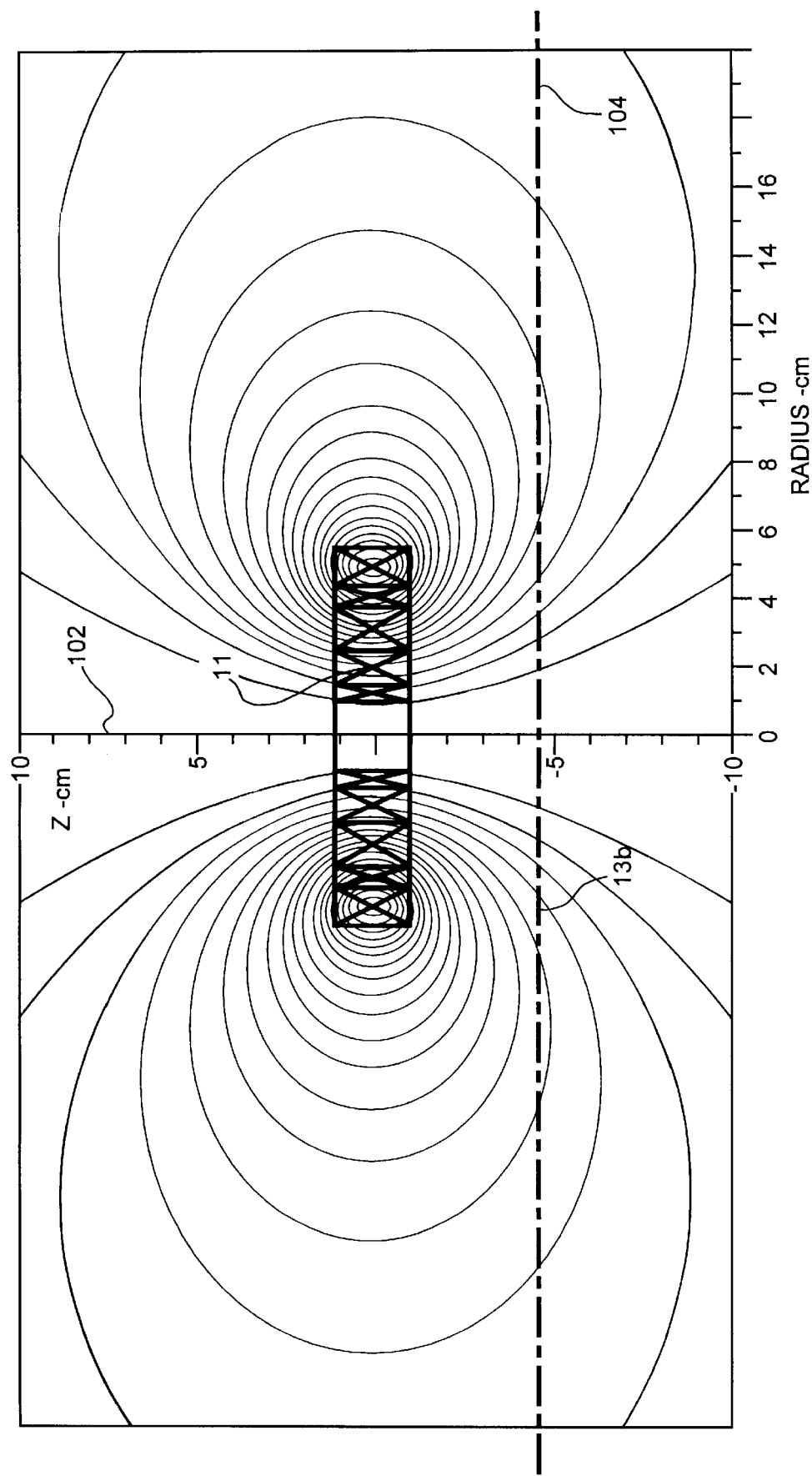
FIG. 2 is a section of the topical magnet with the field lines depicted.
Figure 3:
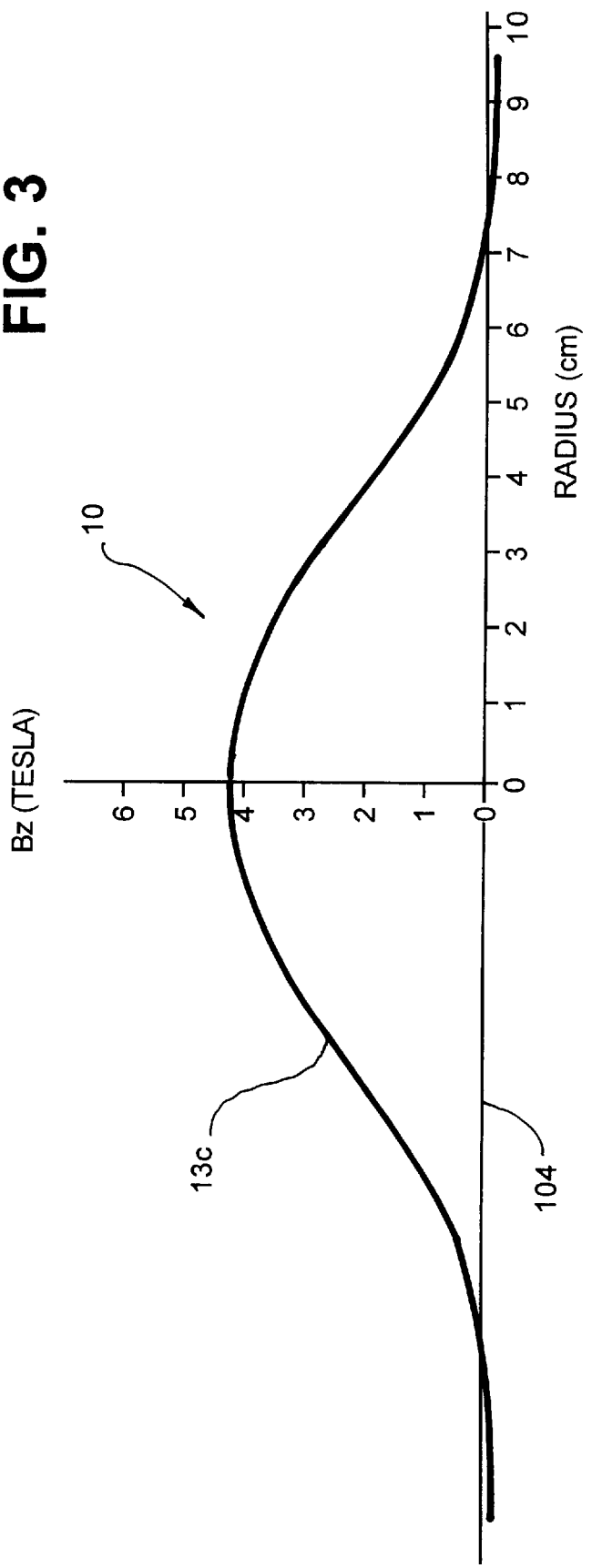
FIG. 3 shows the magnetic field component along a magnet axis.

The topical magnet 11 shown in FIG. 1 is also shown in FIG. 2 with a cross section of the magnetic field lines indicated. The component 10 of the magnetic field which is in the plane including the magnet central axis 102 is shown in FIG. 3 along a vector 104 which passes 4.5 cm in the 102 direction from the magnet center. Subtracting 1 cm of magnet along 102 and 0.5 cm of magnet cryostat along 102 puts axis 104 at 3 cm into the body 23. The magnetic field component 10 has a magnetic field gradient component 10a along axis 104, which is shown in FIG. 4. These curves were calculated using well validated code.

When the beam vector 101 coincides with the vector 104 then 10 is a magnetic field component across the beam vector 101, and thus across the beam path, and 10a is a magnetic field gradient component along the beam vector 101, and thus along the beam path. Across the beam path means perpendicular to the velocities of the incident photons. Along the beam path means perpendicular to across the beam path.

In the case where the beam vector 101 coincides with the 104 vector, an electron-photon cascade proceeding along the 104 vector encounters a steep positive magnetic field gradient component 10a along the beam path, the steepest point of which is indicated by 13d in FIG. 4. The location of this steepest positive gradient is also indicated as point 13c in FIG. 3, as point 13b in FIG. 2, and, in this case where the beam vector 101 coincides with the 104 vector, is indicated as 13a in FIG. 1.

The dose produced by the electrons in the electron-photon cascade can be calculated for the case with no magnetic field and for the case with a magnetic field using the standard and well validated EGS-4 code. The ratio of the dose for the case with a magnetic field relative to the dose for the case with no magnetic field is the relative dose. A relative dose profile is all the values of the relative dose along a beam vector such as 101. The relative dose profile 30 from a 2 cm diameter, 24 MEV photon beam along the beam vector 101 coinciding with the 104 vector is shown in FIG. 5.

As a photon beam enters a body an electron-photon cascade is generated. The dose builds up as more and more electrons enter the cascade by the Compton effect and by pair production. (Again, the differences in charge and particle interactions between electrons and positrons are minimal in the phenomena relied on here so positrons created by pair production are called simply electrons here.) This build up can reach a quasi-equilibrium where the energy carried by electrons into given volume is equal to the energy carried by electrons out of the volume.

As the electrons near the location of the steepest positive magnetic field gradient 13a, at 9.5 cm in FIG. 5, then the increasing Lorentz force from the magnetic field component across the beam path (10 in this case) causes the electron paths to rapidly tighten into decaying spirals and these electrons contribute to the increased relative dose, indicated by the peak 31 in the relative dose profile 30. The Lorentz force from the magnetic field component across the beam path also causes electrons which enter the cascade to rapidly tighten into decaying spiral paths and also contribute to the increased relative dose.

The dose then declines along vector 101 because only electrons just entering the electron-photon cascade are available to contribute to the dose. A minimum in the relative dose, indicated by the valley 32, in the relative dose profile 30 occurs in the vicinity of the steepest negative magnetic field gradient component 14. Further along the beam vector 101 in the valley 32 the decreasing Lorentz force releases electrons from the spiral paths and the electron-photon cascade again builds up.

At a point along a beam vector, 101 for example, chosen to represent the beam, the dose comes from the electron-photon cascade in the beam passing the point, the beam being defined by all of the paths of the incident photons. The relative dose at a point along a beam vector chosen to represent the beam is the ratio of the dose at the point with a magnetic field relative to the dose at the point without any magnetic field.

The relative dose profile, 30 for example, is the curve showing the relative dose at all points along the beam vector in the body. In the relative dose profile 30 the dose received in a target volume located about 10 cm into the body where the relative dose peaks 31 is about 45% greater with the magnetic field than without any magnetic field. Similarly, the dose received in a protected volume located about 19 cm into the body where the dose bottoms 32 is about 35% less with the magnetic field than without any magnetic field. (The central axis 102 of the magnet passes through a point located at 15.5 cm into the body.)

The dose enhancement is the net ratio of the highest dose in a target volume relative to the lowest dose in a protected volume, which is the difference between the highest relative dose, 31 for example, and the lowest relative dose, 32 for example. A relative dose profile thus comprises the dose enhancement and the locations of the greatest relative dose and the least relative dose.

The dose enhancement shown in FIG. 5 is about two. This means that the dose received in a target volume located about 10 cm into the body along the beam vector 101 where the relative dose peaks 31 is about twice the dose received in a protected volume located about 19 cm into the body along the beam vector 101 where the relative dose bottoms 32.

When the beam vector 101 coincides with the 104 vector, then the magnetic field component across the beam path is that shown as 10 in FIG. 3, the magnetic field gradient component along the beam path is that shown as 10a in FIG. 4, and the relative dose profile is that shown as 30 in FIG. 5. The portion of the relative dose profile which is greater than unity can be located outside a target body in a second body in front of the target body so that the protected volume is at the surface of the target body. Also, the portion of the relative dose profile less than unity can be chosen within in the target body.

When the beam vector does not coincide with the 104 vector, such as the beam vector 103 shown in FIG. 1 which is skewed relative to the 104 vector, but there is still a magnetic field component across the beam path and a magnetic field gradient component along the beam path, then the relative dose profile can have a peak followed by a valley like that shown in FIG. 4, can have a peak only (for example when the negative magnetic field gradient component occurs outside the body), can have a valley only (for example when the peak occurs in a second body located before the beam enters the body), and even can have a valley followed by a peak (for example when the beam axis is parallel to the 102 axis).

The topical magnet depicted in FIG. 2 has a thickness of 2 cm and an overall radius of 5.5 cm. It is an array of five concentric coils on a planar surface, with the inner and outer radii of the first coil being 1 cm and 1.5 cm, of the second coil being 1.5 cm and 2.5 cm, of the third coil being 2.5 cm and 3.8 cm, of the fourth coil being 3.8 cm and 4.5 cm, and of the fifth coil being 4.5 cm and 5.5 cm. The magnetic field and magnetic field gradients depicted in FIG. 3 and FIG. 4 and the dose enhancement depicted in FIG. 5 were calculated for this magnet with the coils fabricated of Nb3Sn wire which can carry 2,000 Amps per square millimeter at 2.2 degrees Kelvin and can sustain 14 Tesla fields without quenching. This magnet can produce a magnetic field component across the beam path of slightly over 2 Tesla and with a magnetic field gradient component along the beam path of just under 1 Tesla per centimeter at the point 13b in FIG. 2 which is 3 cm into the body 23 along the magnet central axis 102.

In tissue, the range in centimeters of an electron is approximately ½ the kinetic energy of the electron in MEV. Thus a 10 MEV electron has a range of 5 cm and a 20 MEV electron has a range of 10 cm. The Lorentz force from a magnetic field perpendicular to the velocity of an electron deflects the electron to a decaying spiral path with an initial radius which is approximately the kinetic energy of the electron divided by three times the magnetic field in Tesla. Thus the 10 MEV electron which had a range of 5 cm with no magnetic field has a decaying spiral path with an initial radius of about 1.67 cm in the 2 Tesla field.

For a given energy photon beam, given beam cross section area, and given beam divergence, the relative dose profile, such as 30, is determined by the magnetic field configuration of a topical magnet, such as the topical magnet 11. This magnetic field configuration is determined by the shape of the topical magnet, by the location of the topical magnet relative to the beam path, by the orientation of the topical magnet relative to the beam path, by the shapes, locations, and orientations of magnet coils comprising the topical magnet, and by the currents in the coils.

Thus a relative dose profile from a photon beam can be controlled by control of a magnetic field configuration relative to the beam path. This magnetic field configuration is controlled by control of the position of a topical magnet, control of the orientation of the topical magnet, by control of the currents in magnet coils comprising the topical magnet, and by control of shapes, locations, orientations, and currents of the coils. Thus, photon beam users can choose a relative dose profile and configure a topical magnet magnetic field to produce that relative dose profile.

The relative dose profile can be changed to alternative relative dose profiles during beam use by changes of the magnetic field configuration. For example, a second relative dose profile can be caused by a second magnetic field configuration having a second magnetic field component across the beam path and having a second magnetic field gradient component along the beam path. This can be done during a beam exposure and between exposures when the beam use comprises a series of beam exposures. Control of the relative dose profile by control of the configuration of a topical magnet magnetic field and change of the relative dose profile during beam use does not interfere with any other devices and methods used with a photon beam. Thus, photon beam users can now choose a relative dose profile and can choose changes of the relative dose profile during beam use, both choices specifically tailored to the needs of the beam use.

Results similar to those shown and described above for topical magnet 11 are obtained with other topical magnets. Topical magnets can be made of single coils and of various arrays of magnet coils to produce useful magnetic field configurations. Magnet coils can be arrayed in concentric arrays as shown in FIG. 2 and can be arrayed in non-concentric arrays. Coils can be arrayed in concentric and non-concentric arrays on planer surfaces such as in FIG. 2 and on non-planar surfaces. Coils in these arrays can be spatially separated. Arrays of superconducting magnet coils small enough so that, along with their cryostats, they can be placed inside a living body have been devised.

Other equivalent forms for the topical magnet and other equivalent ways to configure the magnetic field will be obvious hereafter to persons skilled in the art. Therefore this invention is not limited to the particular examples shown and described here.

I claim:

1. In a radiation system, the radiation system having a photon beam source which provides a photon beam incident on a body along a beam path, the photon beam generating an electron-photon cascade along the beam path in the body, a dose enhancement control device comprising a topical magnet, the topical magnet having a magnetic field configuration with a magnetic field component across the beam path and with a magnetic field gradient component along the beam axis which cause a relative dose profile, the relative dose profile being controlled by control of the magnetic field configuration.

2. The device of claim 1 wherein a second relative dose profile is caused during use of the photon beam by a second magnetic field configuration having a second magnetic field component across the beam path and a second magnetic field gradient along the beam path.

3. The device of claim 1 wherein the topical magnet comprises an array of magnet coils.

4. The device of claim 3 wherein the array of magnet coils is a concentric array on a planar surface.

5. The device of claim 3 wherein the array of magnet coils is a concentric array on a non-planar surface.

6. The device of claim 3 wherein the array of magnet coils is a non-concentric array on a planar surface.

7. The device of claim 3 wherein the array of magnet coils is a non-concentric array on a non-planar surface.

8. In a radiation system, the radiation system having a photon beam source which provides a photon beam incident on a body along a beam path, the photon beam generating an electron-photon cascade along the beam path in the body, dose enhancement control means comprising topical means for producing a magnetic field configuration with a magnetic field component across the beam path and with a magnetic field gradient component along the beam path which cause a relative dose profile, the relative dose profile being controlled by control of the magnetic field configuration.

9. The device of claim 8 wherein a second relative dose profile is caused during use of the photon beam by a second magnetic field configuration having an second magnetic field component across the beam path and having a second magnetic field gradient component along the beam path.

10. The device of claim 8 wherein the topical means comprises an array of magnet coils.

11. The device of claim 10 wherein the array of magnet coils is a concentric array on a planar surface.

12. The device of claim 10 wherein the array of magnet coils is a concentric array on a non-planar surface.

13. The device of claim 10 wherein the array of magnet coils is a non-concentric array on a planar surface.

14. The device of claim 10 wherein the array of magnet coils is a non-concentric array on a non-planar surface.

15. A dose enhancement method used in a radiation system, the radiation system having a photon beam source which provides a photon beam incident on a body along a beam path, the photon beam generating an electron-photon cascade along the beam path in the body, the dose enhancement method comprising the steps:

choosing a relative dose profile;

configuring a topical magnet to have a magnetic field configuration with a magnetic field component across the beam path and with a magnetic field gradient component along the beam path which cause the relative dose profile, the relative dose profile being controlled by control of the magnetic field configuration.

16. The method of claim 15 further comprising the steps:

choosing a second relative dose profile; and reconfiguring the topical magnet during use of the photon beam to have a second magnetic field configuration with a second component across the beam path and with a second magnetic field gradient along the beam path to cause the second relative dose profile.

17. The method of claim 15 wherein configuring the topical magnet comprises configuring a magnetic field of an array of magnet coils.

18. The method of claim 17 wherein configuring the magnetic field comprises configuring the magnetic field of an array of concentric magnet coils on a planar surface.

19. The method of claim 17 wherein configuring the magnetic field comprises configuring the magnetic field of an array of concentric magnet coils on a non-planar surface.

20. The method of claim 17 wherein configuring the magnetic field comprises configuring the magnetic field of a non-concentric array of magnet coils on a planar surface.

21. The method of claim 17 wherein configuring the magnetic field comprises configuring the magnetic field of a non-concentric array of magnet coils on a non-planar surface.

* * * * *